United States Patent [19]

Chang

[11] 4,358,950
[45] Nov. 16, 1982

[54] DETECTING NO$_x$ USING THIN FILM ZINC OXIDE SEMICONDUCTOR

[75] Inventor: Shih-Chia Chang, Troy, Mich.

[73] Assignee: General Motors Corporation, Detroit, Mich.

[21] Appl. No.: 227,748

[22] Filed: Jan. 23, 1981

[51] Int. Cl.$^3$ .......................................... G01N 27/04
[52] U.S. Cl. ..................................................... 73/23
[58] Field of Search ............. 73/23, 27 R; 324/71 SN; 338/34; 340/634; 422/88, 98

[56] References Cited

U.S. PATENT DOCUMENTS 4,169,369 10/1979 Chang ..................................... 73/23

OTHER PUBLICATIONS

N. Ichinose et al., "Ceramic Oxide Semiconductor Elements for Detecting Gaseous Components", *Ceramics*, 11 (3), pp. 203–211, 1976.
T. Seiyama et al., "Study on a Detector for Gaseous Components Using Semiconductive Thin Films", *Analytical Chemistry*, vol. 38, No. 8, pp. 1069–1073, Jul. 1966.

*Primary Examiner*—Stephen A. Kreitman
*Attorney, Agent, or Firm*—Douglas D. Fekete

[57] ABSTRACT

A method for detecting NO$_x$ species in an oxygen-containing gas comprises measuring the electrical resistance of a thin film of oxygen-deficient zinc oxide exposed to the sample.

4 Claims, 3 Drawing Figures

DETECTING $NO_x$ USING THIN FILM ZINC OXIDE SEMICONDUCTOR

BACKGROUND OF THE INVENTION

This invention relates to measuring the concentration of nitrogen oxide compounds ($NO_x$) in a gaseous mixture using a solid state sensing element comprising a semiconductive zinc oxide thin film.

The emission of gaseous nitrogen oxide compounds, particularly from automotive internal combustion engines, is a major environmental concern. Several nitrogen oxide compounds have been identified and are generally referred to as a group by the symbol "$NO_x$". The most significant are nitric oxide (NO) and nitrogen dioxide ($NO_2$).

To better study and monitor $NO_x$ emissions, an instrument is desired that provides accurate, continuous readings directly from a sample gas without pretreatment or reagents and without interference from other sample constituents. It is known that the electrical resistance of a thin film of a semiconductive material exposed to a gaseous mixture may be affected by the presence of certain species, depending upon the material, the species and the composition of the mixture. U.S. Pat. No. 4,169,369, issued to the present inventor and coassigned, describes a $NO_x$ sensor having a semiconductive tin oxide thin film. Zinc oxide, iron oxide, lead oxide and cadmium oxide also form N-type thin film semiconductors that are sensitive to common reducing and oxidizing gaseous species in an inert gas. However, it is not possible to predict the effect of a particular species upon the thin film in the presence of a relatively high concentration of another species to which the film is sensitive. In contrast to tin oxide, it has been found that iron oxide, lead oxide and cadmium oxide are essentially insensitive to $NO_x$ in air. Apparently, the relatively high oxygen concentration saturates the thin film surface so that any interaction with $NO_x$ species is too small for detection. In view of this, it is totally unexpected that a zinc oxide sensor could be adapted to measure $NO_x$ concentration in the presence of a relatively high oxygen concentration, such as in air, or other oxidizing or reducing species.

It is an object of this invention to provide a method for detecting $NO_x$ in a gaseous mixture utilizing a semiconductive zinc oxide thin film to make relatively rapid, direct readings without sample pretreatment or reagent additions, which readings produce an accurate measurement of the $NO_x$ concentration despite a relatively large concentration of oxygen in the mixture and further despite the presence of other oxidizing and reducing species, including hydrogen and propylene, in the mixture.

SUMMARY OF THE INVENTION

In a preferred embodiment, $NO_x$ is quantitatively detected in a gaseous sample by measuring the resistance of a thin film of semiconductive zinc oxide exposed to the sample. The thin film is prepared by RF sputtering onto an inert substrate from a sintered zinc oxide target and thereafter heat treating in air between 400° and 500° C. When exposed to the sample, the film is heated between about 270° to 300° C. and the resistance is measured between spaced electrodes using a suitable ohmmeter. It has been found that the logarithm of the resistance is directly proportional to the logarithm of the $NO_x$ concentration in the sample. Thus, the $NO_x$ concentration of an unknown sample can be determined by comparing the measured value with values obtained from known mixtures. Further, the sensor responds to the $NO_x$ concentration even in a sample having a substantial oxygen concentration and optionally containing other common oxidizing and reducing gases. Thus, the sensor is useful for measuring $NO_x$ in air or particularly in automotive exhaust gases diluted with air.

While I do not wish to be limited to any particular theory, it is believed that the $NO_x$-sensitive zinc oxide has an oxygen to zinc ratio less than the ZnO stoichiometric ratio, that is, less than one. This oxygen deficiency results in defects in the zinc oxide crystalline structure, which supply electrons for conduction through the crystal. Thus, zinc oxide is an N-type semiconductor. It is also believed that sensor operation is based upon a chemisorption phenomenon. $NO_x$ species are absorbed onto the zinc oxide film surface and alter the electron conduction properties of defects near the surface. For a thin film, this $NO_x$-defect interaction has a significant and observable affect upon bulk electrical properties, particularly upon resistance. The amount of gas absorbed, and thus the effect upon resistance, depends upon the $NO_x$ concentration. The sensor responds to the gas until a concentration is reached at which the chemisorption sites are substantially saturated and a maximum number of defects are effected. Since semiconductive zinc oxide thin films are sensitive to oxygen, a high concentration of oxygen, such as in air, saturates the chemisorption sites and would be expected to have such a substantial effect upon the film that any interaction with a small amount of a second oxidizing species would be masked. Surprisingly, a substantial $NO_x$-film interaction has been found that is clearly observable even when oxygen saturated. For example, less than about 4 ppm nitrogen dioxide in air increases the resistance by an order of magnitude. Thus, the method of this invention is capable of detecting trace $NO_x$ levels (ppm) in air (21 percent oxygen).

DETAILED DESCRIPTION OF THE INVENTION

Figure 1:
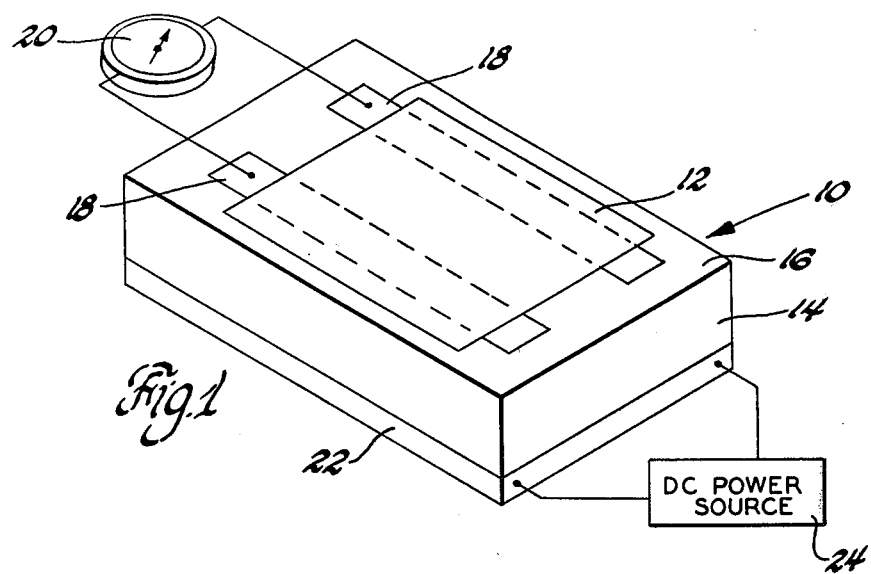
FIG. 1 is a perspective view of a solid state semiconductor sensor of this invention.

Referring to FIG. 1, a sensing element 10 comprising a semiconductive zinc oxide thin film 12 is illustrated for measuring $NO_x$ in a gaseous mixture in accordance with a preferred embodiment of this invention. Sensor 10 comprises an alumina body 14 having dimensions of approximately 5 mm×5 mm×0.5 mm. Alumina is preferred because it is a good electrical insulator, but has adequate thermal conduction to provide uniform heating of sensor 10. Body 14 has a first major surface 16 having a surface finish (the perpendicular distance between the levels of the highest peak and lowest valley) of approximately 400 A°. It is believed that the roughness of surface 16 increases the surface area of an applied film and enhances defects in the film to improve $NO_x$ sensitivity.

Two opposite, parallel gold-glass electrodes 18 having dimensions of 1 mm × 2 mm are applied to surface 16 using silk screen technology and fired. Electrodes 18 are spaced apart by approximately 1.5 mm. Electrodes 18 are connected to a low power ohmmeter 20 that measures the resistance of film 12 utilizing a substantially constant current of about one microampere. Maintaining sensor 10 at a constant temperature is critical to making accurate measurements. Since current passing through a resisting material generates heat, the use of a small constant current is preferred to avoid temperature fluctuations.

A resistance heater 22 is applied to body 14 opposite surface 16. The heater material displays a relatively constant and temperature-independent resistance at $NO_x$-sensing temperatures. Adjacent corners of heater 22 are connected to a conventional DC power source 24. A chromel-constantan thermocouple (not shown) is attached to the heater surface to provide a suitable signal for electrically controlling power source 24 and thereby maintaining sensor 10 at a desired temperature.

Zinc oxide film 12 is applied to surface 16 over electrodes 18 and is continuous between the electrodes. Film 12 is deposited by RF sputtering from a sintered zinc oxide target in a low pressure oxygen-argon atmosphere. The target is prepared by pressing zinc oxide powder with a suitable organic binder and sintering to vaporize the binder and fuse the powder. A mask is used to control the region of deposition. Within a RF discharge plasma apparatus, substrate 14 is positioned on one electrode with surface 16 facing the target positioned upon the second electrode. The substrate-target distance is about 7.6 cm. The atmosphere contains approximately 8 millitorr partial pressure argon and approximately 2 millitorr partial pressure oxygen. The RF plasma is generated with a forward power of 400 watts and an accelerating voltage of 2.2 kilovolts (the target being cathodic). During sputtering, the temperature of substrate 14 does not exceed 200° C. Under these conditions, a suitable film is deposited after about 10 minutes. The deposited zinc oxide film is stabilized by heating in air at between 400° to 500° C. for two hours to optimize $NO_x$ sensitivity. The product zinc oxide thin film 12 is approximately 1000 Å thick.

Figure 2:
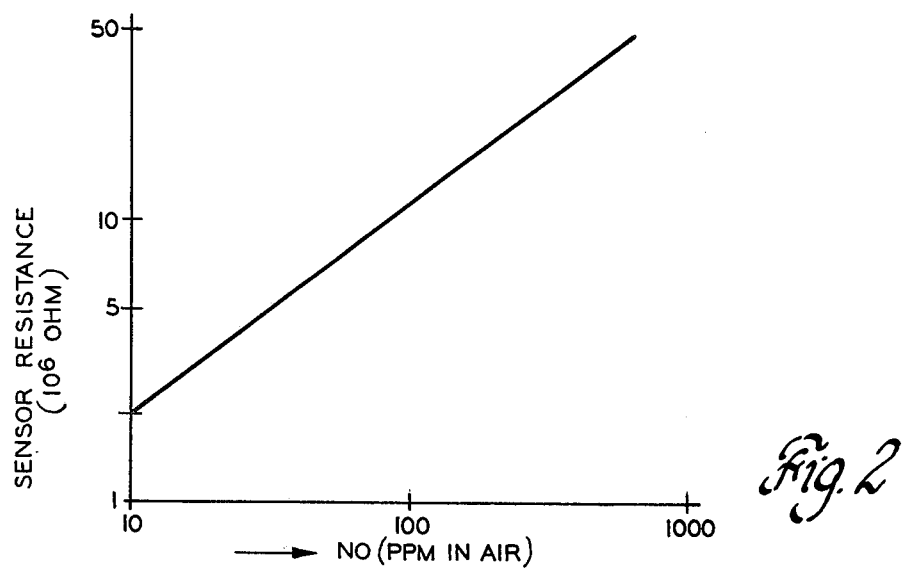
FIG. 2 is a graph on log-log coordinates of electrical resistance of a zinc oxide thin film as a function of concentration of nitric oxide (NO) in air.

A sensor 10, prepared as described hereinabove, was tested by exposing to a gaseous sample in an airtight container. The samples consisted of room temperature air to which known nitric oxide (NO) additions were made. Heater 22 maintained the sensor temperature at about 300° C. The film resistance in the blank air sample (no NO added) was about $1.75 \times 10^6$ ohm. FIG. 2 shows the film resistance as a function of the NO concentration, plotted on log-log coordinates. As seen, up to at least 1000 ppm, the logarithm of the sensor resistance increases linearly with the logarithm of the nitric oxide concentration. Further, an increase in NO concentration from 100 to 1000 ppm increases the sensor resistance by about $5 \times 10^7$ ohms, a substantial increase in view of the blank resistance. In these experiments, the sample was prepared and the sensor then introduced into the container. Response time was typically about 2 minutes. The recovery time; i.e., the time after the container was vented until the thin film sensor returned to the blank value, was typically 8 minutes.

Figure 3:
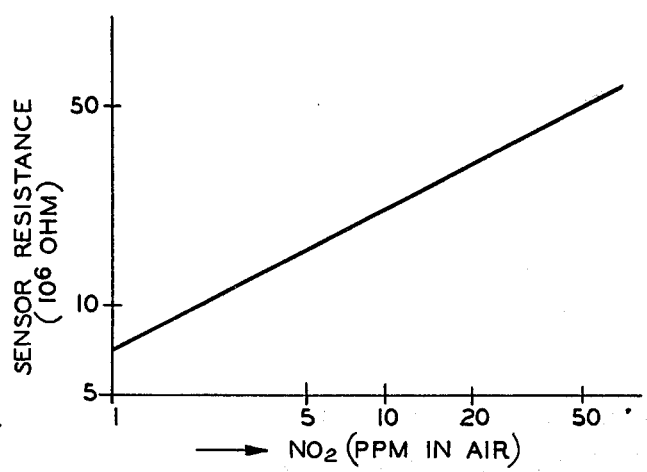
FIG. 3 is a graph on log-log coordinates of electrical resistance of a zinc oxide thin film as a function of concentration of nitrogen dioxide ($NO_2$) in air.

A sensor was similarly tested by heating at 300° C. and exposing to room air samples containing known nitrogen dioxide ($NO_2$) additions. The results are depicted in FIG. 3. The film resistance in the blank air sample (no $NO_2$) was about $1.25 \times 10^6$ ohms. The logarithm of the sensor resistance increases linearly with the logarithm of the nitrogen dioxide concentration. An increase from 5 ppm to 50 ppm increases the resistance by about $4.5 \times 10^7$ ohms. It is noted that the film is substantially more sensitive to nitrogen dioxide than to nitric oxide. A resistance increase of one order of magnitude above the blank value requires about 3 ppm nitrogen dioxide, compared to about 175 ppm nitric oxide.

Sensor response to common reducing gases was also determined. A sensor was exposed to 20 ppm nitrogen dioxide and was essentially unaffected by additions of up to 250 ppm of hydrogen and propylene. The effect was estimated to be less than 1%. Water vapor affects the reading, but this effect is believed to be small in comparison to the $NO_x$ response.

In the described embodiment, the zinc oxide film thickness was 1000 Å and the substrate finish was about 400 Å. The roughness of the substrate surface enhances defects in the film that interact with chemisorbed $NO_x$ species. Film thickness and surface finish are interrelated parameters. Preferably, the film is sufficiently thick and the surface finish sufficiently smooth to produce a continuous film. However, a substrate surface that is too smooth provides insufficient lattice defects. If the film is too thick, the $NO_x$-defect interactions, which occur near the film surface, do not have a measurable effect upon the overall film resistance. In general, substrates having surface finishes ranging between 300 to 4000 Å are suitable for use with zinc oxide film ranging between 600 and 10,000 Å.

The $NO_x$ sensitive zinc oxide film is preferably deposited upon the substrate by sputtering from a zinc oxide target in an argon-oxygen atmosphere. $NO_x$ sensitivity is enhanced by heating the sputtered film in air prior to its use. This heat treatment stabilizes the oxygen content and also its resistance. Suitable film stabilization is afforded by heating the sensor to a temperature preferably between 400 to 500° C. Although a sputtered film is preferred, films having similar $NO_x$ characteristics may be produced by metal vapor deposition followed by oxidation or by the application of a suitable slurry followed by evaporation.

Materials other than those mentioned above may be used to manufacture the substrate and the electrodes without significantly affecting the performance of the zinc oxide thin film. For example, other inert, refractory materials, such as steatite, are good electrical insulators and form suitable sensor bodies. Any good electrical conductor may be used for the electrodes. The heater need not be attached to the sensor. Attaching the heater as in the preferred embodiment permits the sensor to be maintained at a desired temperature without heating the entire sample. It has been found that the most accurate readings are obtained by operating the sensor between about 250° to 325° C., preferably between 270° to 300° C. Operated above that temperature range, the sensor responds faster, but typically overshoots. When the sensor is operated below that range, a slow response is obtained that typically represents too low a concentration.

Although this invention has been described in terms of certain embodiments thereof, it is not intended that it be limited to the above description but rather only to the extent set forth in the claims that follow.

The embodiments of the invention in which an exclusive property or privilege is claimed are defined as follows:

1. A method for detecting the presence of a nitrogen oxide compound in an oxygen-containing atmosphere comprising measuring the electrical resistance of a zinc oxide thin film semiconductor exposed to said atmosphere, said zinc oxide having an electrical resistance that is sensitive to ambient nitrogen oxide compounds, said film having a predetermined resistance when exposed to a like oxygen-containing gas free of nitrogen oxide compounds, whereby the presence of nitrogen oxide compounds in the atmosphere is indicated by a substantial increase in the film resistance over said nitrogen oxide-free value.

2. A method for detecting the presence of $NO_x$ species in an oxygen-containing gaseous mixture comprising exposing to the mixture a thin film composed of an oxygen-deficient zinc oxide material having an electrical resistance that is influenced by $NO_x$ species, said film being maintained at a temperature between 250° and 325° C., measuring the electrical resistance of the film while exposed to the mixture, and utilizing the measured resistance value to determine the $NO_x$ concentration in the mixture.

3. A method for determining the concentration of nitric oxide or nitrogen dioxide, or both, in a gaseous mixture containing oxygen in an amount substantially greater than the nitrogen oxygen compound, said method comprising sputtering zinc oxide material from a zinc oxide target onto an inert substrate to form thereon a continuous thin film that is between about 600 to 10,000 Å thick, heating the sputtered film in air between 400° to 500° C. for a sufficient time to stabilize the oxygen content at an oxygen-to-zinc ratio less than a stoichiometric one, said oxygen-deficient zinc oxide material being adapted to conduct electrons with a measurable resistance and to interact with ambient nitrogen oxygen compound in a manner that affects the resistance, contacting the film with spaced electrodes arranged so as to allow an electrical resistance of the film to be measured across a path generally parallel to the film surface, exposing the film to said mixture while heating between about 270° to 300° C., whereupon nitrogen oxygen compound interact with said film and alter the resistance thereof, measuring the resistance of the film between said electrodes, and comparing the measured resistance to similar resistance values obtained for gases having known nitrogen oxygen compound concentrations to determine the concentration in said mixture.

4. The method for detecting the presence of $NO_x$ species in an oxygen-containing gaseous mixture comprising exposing a thin film composed of a sputtered and heat-treated zinc oxide material to the mixture, said zinc oxide having an electrical resistance that is increased by the presence of gaseous $NO_x$ species in contact therewith, said film being maintained at a temperature between 250° and 325° C., measuring the electrical resistance of the thin film while exposed to the mixture, and utilizing the measured resistance value to determine the $NO_x$ concentration in the mixture.

* * * * *